US010610346B2

(12) United States Patent
Schwartz

(10) Patent No.: US 10,610,346 B2
(45) Date of Patent: Apr. 7, 2020

(54) DELIVERY SYSTEM FOR POSITIONING AND AFFIXING SURGICAL MESH OR SURGICAL BUTTRESS COVERING A SURGICAL MARGIN

(71) Applicant: AcuityBio Corporation, Newton, MA (US)

(72) Inventor: John Schwartz, Newton, MA (US)

(73) Assignee: AcuityBio Corporation, Newtonville, MA (US)

( * ) Notice: Subject to any disclaimer, the term of this patent is extended or adjusted under 35 U.S.C. 154(b) by 204 days.

(21) Appl. No.: 15/281,619

(22) Filed: Sep. 30, 2016

(65) Prior Publication Data

US 2017/0172720 A1 Jun. 22, 2017

Related U.S. Application Data

(63) Continuation of application No. PCT/US2015/024989, filed on Apr. 8, 2015.
(Continued)

(51) Int. Cl.
*A61F 2/00* (2006.01)
*A61B 17/068* (2006.01)
(Continued)

(52) U.S. Cl.
CPC .......... *A61F 2/0063* (2013.01); *A61B 17/068* (2013.01); *A61F 13/00063* (2013.01);
(Continued)

(58) Field of Classification Search
CPC ........ A61F 2/00; A61F 2/0063; A61B 17/068; A61B 17/122; A61B 17/00234
See application file for complete search history.

(56) References Cited

U.S. PATENT DOCUMENTS 3,875,937 A 4/1975 Schmitt et al.
3,937,223 A 2/1976 Roth
(Continued)

FOREIGN PATENT DOCUMENTS

EP 2505164 A1 10/2012
EP 2559387 A1 2/2013
(Continued)

OTHER PUBLICATIONS

International Search Report and Written Opinion issued for International Application No. PCT/US2015/24989, dated Jul. 13, 2015.
(Continued)

*Primary Examiner* — Vi X Nguyen
(74) *Attorney, Agent, or Firm* — McCarter & English, LLP

(57) ABSTRACT

Embodiments include a surgical implant delivery system for positioning and affixing a surgical implant (e.g., a surgical mesh, a surgical buttress, etc.) covering a surgical margin. The system includes a cartridge releasably holding the surgical implant and a plurality of fixation elements associated with the surgical implant. The system also includes an introducer having an elongate body, a head pivotably coupled to receive the cartridge forming a combined head and cartridge, and a handle including a grip and an in-line trigger. The introducer also includes an actuation mechanism connected with the in-line trigger of the handle configured to affix the surgical implant to the surgical margin using the one or more fixation elements.

26 Claims, 7 Drawing Sheets

Related U.S. Application Data

(60) Provisional application No. 61/977,033, filed on Apr. 8, 2014.

(51) Int. Cl.
*A61L 31/16* (2006.01)
*A61F 13/36* (2006.01)
*A61F 13/00* (2006.01)
*A61B 17/064* (2006.01)

(52) U.S. Cl.
CPC .............. *A61F 13/36* (2013.01); *A61L 31/16* (2013.01); *A61B 2017/0641* (2013.01); *A61B 2017/0647* (2013.01); *A61F 2002/0072* (2013.01); *A61F 2210/0004* (2013.01); *A61F 2250/0067* (2013.01)

(56) References Cited

U.S. PATENT DOCUMENTS

| | | | |
|---|---|---|---|
| 4,128,612 | A | 12/1978 | Roth |
| 5,405,360 | A | 4/1995 | Tovey |
| 7,671,095 | B2 | 3/2010 | Colson et al. |
| 8,460,171 | B2 | 6/2013 | von Pechmann et al. |
| 8,535,260 | B2 | 9/2013 | Kassab et al. |
| 8,584,920 | B2 | 11/2013 | Hodgkinson |
| 8,617,188 | B2 | 12/2013 | Dudai |
| 8,668,129 | B2 | 3/2014 | Olson |
| 2007/0246505 | A1 | 10/2007 | Pace-Floridia et al. |
| 2008/0188874 | A1 | 8/2008 | Henderson |
| 2010/0280309 | A1 | 11/2010 | von Pechmann |
| 2010/0312357 | A1 | 12/2010 | Levin et al. |
| 2011/0040311 | A1 | 2/2011 | Levin et al. |
| 2011/0172785 | A1 | 7/2011 | Wolinsky et al. |
| 2012/0253339 | A1 | 10/2012 | Rick et al. |
| 2012/0289980 | A1 | 11/2012 | Ostrovsky et al. |
| 2013/0068820 | A1* | 3/2013 | Miller .............. A61B 17/00491 227/180.1 |

FOREIGN PATENT DOCUMENTS

| | | |
|---|---|---|
| WO | 2006082587 A2 | 8/2006 |
| WO | 2008057281 A2 | 5/2008 |
| WO | 2011043795 A1 | 4/2011 |
| WO | 2011/145091 A1 | 11/2011 |

OTHER PUBLICATIONS

International Preliminary Report on Patentability isued for International Application No. PCT/US2015/024989 dated Oct. 12, 2016.
Supplementary European Search Report for Application No. 15775961.4, dated Oct. 10, 2017, 9 pages.
Bard Davol Inc., "Echo PSTM Positioning System" brochure, 2013, 6 pages, U.S.A. (The month of publication is not available; however, the year of publication is sufficiently earlier than the effective U.S. filing date so that the particular month of publication is not an issue.).
Covidien, "AccumeshTM Positioning System" brochure, 2012, 3 pages, U.S.A. (The month of publication is not available; however, the year of publication is sufficiently earlier than the effective U.S. filing date so that the particular month of publication is not an issue.).

* cited by examiner

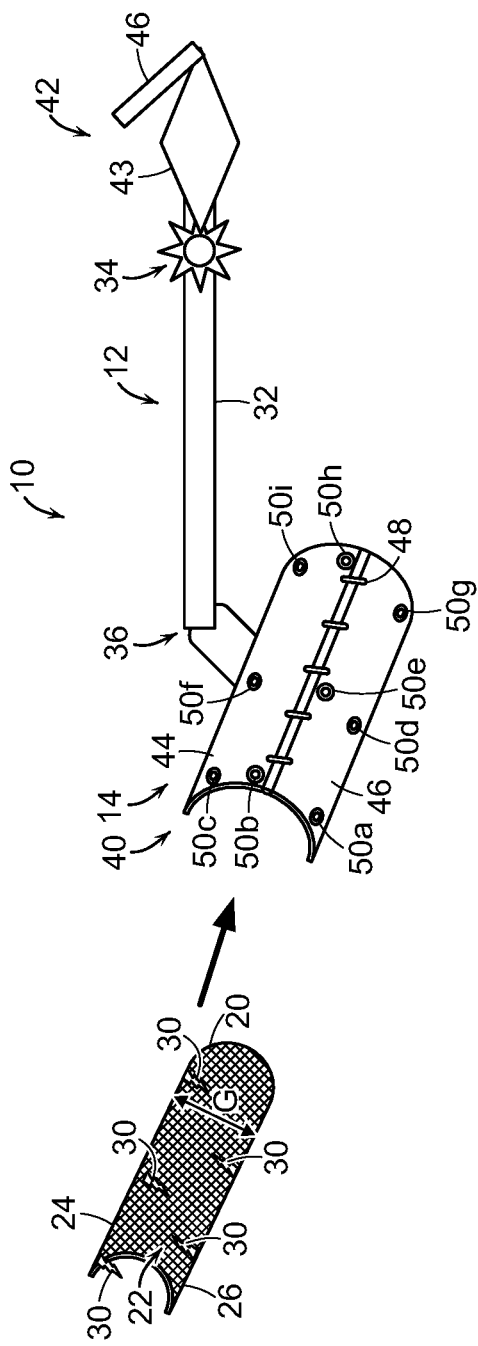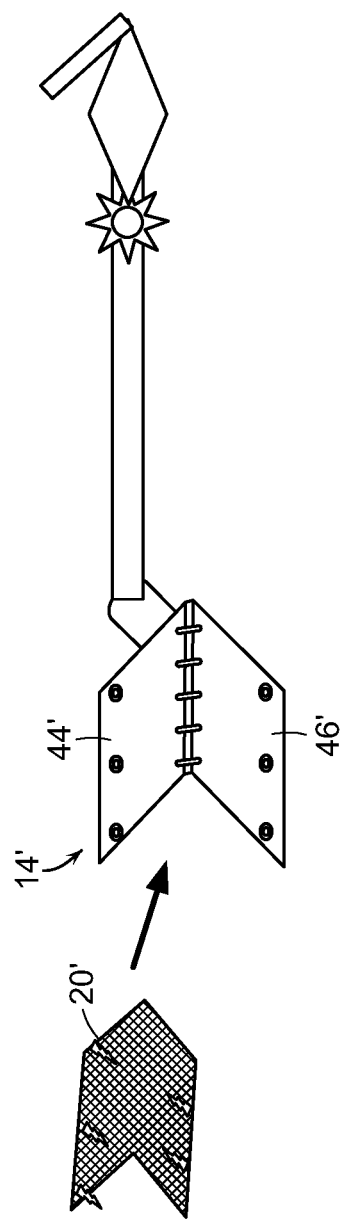

DELIVERY SYSTEM FOR POSITIONING AND AFFIXING SURGICAL MESH OR SURGICAL BUTTRESS COVERING A SURGICAL MARGIN

RELATED APPLICATIONS

This application is a continuation under 35 U.S.C. § 111(a) of International Application No. PCT/US2015/024989, filed Apr. 8, 2015, which claims priority to U.S. Provisional Application No. 61/977,033, filed Apr. 8, 2014, the contents of both of which are incorporated by reference herein in their entireties.

FIELD OF INVENTION

Some embodiments of the invention relate to a system, apparatus and method for applying a surgical fabric, surgical mesh, or surgical buttress to body tissues, and more particularly, to a system apparatus, and method for applying and affixing a biocompatible and/or biodegradable, surgical fabric, surgical mesh, or surgical buttress covering a surgical margin.

BACKGROUND

The sustained delivery of pharmaceutical agents with low systemic toxicity is desirable for the treatment of systemic diseases including, but not limited, to malignancy and certain infections. Medication can be administered in a variety of ways including orally, aerosolized inhaled, subcutaneously, intramuscularly, intraperitoneally, transcutaneously, and intravenously. Drug delivery refers to approaches, formulations, technologies, and systems for transporting a pharmaceutical compound in the body as needed to safely achieve a desired therapeutic effect. Conventional drug delivery may involve site-targeting within the body or facilitating systemic pharmacokinetics. In either case, conventional drug delivery is typically concerned with both quantity and duration of drug presence.

Unfortunately, systemic administration of drugs can result in unwanted toxicity. Toxicity resulting from the systemic administration of many drugs is often related to total systemic drug exposure. Intravenous and systemic drug therapy most commonly fails due to one or more of poor drug solubility, localized tissue damage upon drug extravasation, short in-vivo stability of drug, unfavorable drug pharmacokinetics, poor biodistribution, and lack of selectivity for disease target. Variability in how individual patients absorb the drug into plasma and clear the drug from systemic circulation may account for a significant component of patient-to-patient differences in toxicity and differences in toxicity for an individual patient from day-to-day. Pharmacokinetic variability may result from day-to-day changes in an individual patient's ability to metabolize or excrete drug, or from between-patient differences in drug metabolism or excretion. Generally, drugs administered intravenously (i.e., through IV) have a relatively limited half-life due to clearance from plasma through protein binding and excretion. The concentration of drug needed to be administered systemically to be effective is typically constrained by the maximum tolerated dose or rate of administration due to systemic toxic effects. This limitation reduces the possibility of delivering a sustained and efficacious drug level due to toxicity. As a result, targeted tissues do not sustain an even level of drug for more than short times. This can lead to undertreatment of target tissue and results in the opportunity to select for the emergence of chemoresistant disease. Localized drug delivery at the site of disease is preferred to reduce off-target systemic toxicity, but has been challenging to achieve.

Many of the pharmacological properties of conventional ("free") drugs can be improved through the use of drug delivery systems providing sustained release of biological and chemotherapeutic agents. Methods of regulated, slow, and localized drug release have considerable pharmacodynamic advantages for increasing the drug's efficacy. Drug delivery can be advanced by controlling the diffusion of drugs through polymeric matrices and/or the degradation of these polymers.

Sustained, localized drug release enables superior patient compliance and patient outcomes by increasing the therapeutic index of drugs. Sustained and slow drug release is usually achieved either by incorporation of a therapeutic drug into an implantable reservoir or by implantation of biodegradable or non-biodegradable materials containing the desired drug. The drug can be actively expelled at a defined rate with a pump. Alternatively, drug can be released passively from the implant by diffusion, erosion, or a combination of the two.

The development of biodegradable chemotherapeutic drug delivery implants is useful for the treatment of localized disease (e.g., malignancy or antimicrobial compounds for treating postsurgical infections or focal infections in immuno-compromised patients, etc.) Efficacies of slow drug release systems are usually determined by measurement of concentrations of the implanted drug in plasma or by assessment of the underlying disease treated (e.g., improving infection or decrease in the size of cancer, prevention of recurrence, etc.). For example, cancer chemotherapy delivery implants placed on a surgical margin would reduce the risk of localized recurrence. Chest wall tuberculosis requires surgical resection in most cases and complete surgical resection may be needed to keep the recurrence rate low. For patients with tuberculosis who undergo surgical resection, localized antimicrobial delivery at the surgical margin would assist in patient treatment compliance, increase treatment efficacy, and reduce the development of drug resistant organisms, as is common in aspergillosis and tuberculosis patients.

In the case of operable lung cancer, when a patient is deemed physiologically healthy, surgical resection is the treatment of choice. The operation for treating lung cancer is typically a pneumonectomy, or lobectomy, anatomic resection along with its vascular supply, and lymphatic drainage and wedge resection. Instead of a pneumonectomy or lobectomy procedure, the physician may choose to perform a wedge resection. Wedge resectioning involves the removal of an irregular triangle-shaped slice of tissue mass including the tumor or lesion, followed by surgical suturing via staple line or the edges of the resection margin are then approximated with a running locked suture to prevent air and blood leaks. In general, repair of the wedge resection is by way of the staple/resection line allowing the underlying organ to retain its shape without distortion. Typically, a wedge resection leaves just a single stitch line or staple line. Despite the advantages concerning the operation procedure, wedge resections have not been considered an acceptable oncological resection method for cancer in patients who are fit physiologically to undergo lobectomies. What makes a wedge resection undesirable in cancer patients is the 19% rate of localized recurrence of cancer at the resection margin.

One method of localized treatment of resection margins used to prevent recurrence is brachytherapy. Brachytherapy involves application of a vicryl patch/mesh, into which brachytherapy seeds are sewn. The biodegradable mesh with radioactive seeds is then affixed to the lung tissue covering the resected area. Such a brachytherapy mesh is introduced though thoracotomy or minimally invasively through intercostal access with video assisted thoracoscopic surgery (VATS) and attached covering a resection staple line. A study found that the wedge and brachytherapy resulted in 1% local recurrence (LR), while wedge alone resulted in a 19% LR (see d'Amato et al., "Intraoperative Brachytherapy Following Thoracoscopic Wedge Resection of Stage 1 Lung Cancer", Chest Off. Pub. Of the Am. Coll. Of Chest Phys., 114(4):1112-5 Oct. 1998). However, despite the finding of positive results regarding the brachytherapy and wedge resection treatment combinations, the procedure has associated disadvantages. First, it is very operator dependent. Second, reproducibility is tedious, especially in video-assisted cases adding an hour or more to the already complicated procedure in physiologically compromised patients. Third, medical staff are irradiated during the surgical preparation and procedure. These disadvantages have prevented the wide adoption of brachytherapy.

In many surgical procedures, including those involved in open and endoscopic surgery, it is often necessary to fasten, staple, suture, glue, clip or clamp tissue together. Clinicians have been clamoring for a method of localized administration of drugs to various resection margins. The difficulty in precise placement of drug at the site of disease and lack of sustained therapeutic concentrations of drug at the site of disease delivered by iv has hampered the ability to deliver localized therapy used to treat malignant and non-malignant diseases. Various exemplary embodiments of the present invention simply and uniquely solve these two presently intractable problems in novel ways.

SUMMARY

Some embodiments include systems, apparatuses and methods designed to accurately and easily deliver a drug-eluting material to a surgical resection margin. In some embodiments, an introducer facilitates the accurate surgical placement of medical implants and drug-eluting materials to resection margins. Ergonomic design of the introducer and ease of accurate placement are important innovations associated with embodiments of the disclosed device placement methods and systems. Efficient placement of localized drug delivery associated with some embodiments would result in reduced hemorrhage, air leaks and fistulas due to the application of supportive material to the resection. Efficient placement of localized drug delivery associated with some embodiments would also enhanced patient survival due to higher efficacy with reduced toxicity due to more efficacious drug administration.

An embodiment includes a surgical mesh delivery system for positioning and affixing a surgical mesh covering a surgical margin. The system includes a cartridge releasably holding a surgical mesh and a plurality of fixation elements associated with the surgical mesh, and an introducer. The surgical mesh has a first surface, a first end portion, and a second end portion. The cartridge positions the first surface at the first end portion of the surgical mesh facing, and separated from, the first surface at the second end portion of the surgical mesh by a gap. The fixation elements are positioned at the first end portion and/or at the second end portion of the surgical mesh.

The introducer includes an elongate body having a proximal end portion and a distal end portion. The introducer also includes a head pivotably coupled to the distal end portion of the elongate body and configured to receive the cartridge forming a combined head and cartridge. The combined head and cartridge is configured to receive the surgical margin in the gap, and configured to position the first surface of the surgical mesh covering the surgical margin. The introducer also includes a handle connected with the proximal end portion of the elongate body, the handle including a grip and an in-line trigger, an articulation mechanism and an actuation mechanism. The articulation mechanism is configured to articulate the combined cartridge and head relative to the elongate body using the handle. The actuation mechanism is configured to affix the surgical mesh to the surgical margin using the one or more fixation elements. In some embodiments, the actuation mechanism is connected with an inline trigger of the handle.

Another embodiment includes a surgical mesh delivery system for positioning and affixing a surgical mesh covering a surgical margin. The system includes a cartridge, an introducer, and an actuation mechanism. The cartridge includes a surgical mesh having a first surface, a second surface, a first end portion, and a second end portion. The cartridge also includes a clamping element. The clamping element includes a first clamping surface opposite a second clamping surface. The cartridge is configured to hold the surgical mesh in a configuration with the second surface of the surgical mesh at the first end portion in contact with the first clamping surface, with the second surface of the surgical mesh at the second end portion in contact with the second clamping surface, and with the first surface of the surgical mesh at the first end portion facing, and separated from, the first surface of the surgical mesh at the second end portion by a gap. The cartridge is configured to receive the surgical margin in the gap, and configured to position the first surface of the surgical mesh covering the surgical margin. The introducer includes an elongate body having a proximal end portion and a distal end portion. The distal end portion is configured to pivotably and releasably couple with the cartridge. The introducer also includes a handle connected with the proximal end portion of the elongate body, the handle portion including a grip and an in-line trigger. The in-line trigger is connected with the actuation mechanism of the cartridge. The cartridge further includes an articulation mechanism configured to articulate the cartridge relative to the elongate body using the handle. The actuation mechanism is configured to change a spacing of the gap to clamp the surgical mesh to the surgical margin.

BRIEF DESCRIPTION OF THE DRAWINGS

The drawings are intended to illustrate the teachings taught herein and are not intended to show relative sizes and dimensions, or to limit the scope of examples or embodiments. In the drawings, the same numbers are used throughout the drawings to reference like features and components of like function.

FIG. 1 schematically depicts an apparatus for introduction of a surgical mesh having curved jaws and a surgical mesh with one or more fixation elements being loaded into the apparatus, in accordance with an embodiment.

FIG. 2 schematically depicts an apparatus for introduction of a surgical mesh having flat jaws and a surgical mesh with one or more fixation elements being loaded into the apparatus, in accordance with another embodiment.

DETAILED DESCRIPTION

Figure 3:
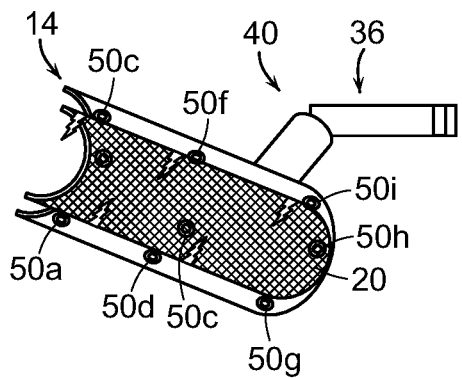
FIG. 3 schematically depicts a head and distal portion of an elongate body of an introducer with a surgical mesh loaded into the head, in accordance with an embodiment.

In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse, or other care provider, and may include support personnel.

Some embodiments described herein can be employed in endoscopic surgery. Endoscopic surgery is one of the truly great advances in recent years to reduce the invasiveness of surgical procedures. Generally, endoscopic surgery involves incising through body walls for example, viewing and/or operating on the ovaries, uterus, gall bladder, bowels, kidneys, appendix, etc. There are many common endoscopic surgical procedures, for example, arthroscopy, laparoscopy (pelviscopy), gastroentroscopy and laryngobronchoscopy.

Some embodiments employ an implantable device (e.g., a surgical material, a surgical buttress, a surgical mesh) of a material sufficiently compliant to enrobe or be affixed to a surgical resection margin. In some embodiments, an implantable device enrobing or affixed to a surgical margin would perform one or more of the following functions: assisting in prevention of blood and air leaks, mechanically support closure of the resection margin, and applying therapeutic microspheres, extruded microparticulates, rods, gels, sheets/films, scaffolds, inserts, foams, or coatings.

In some embodiments, the implanted material is preferably releasably held to surfaces of the apparatus through pins, clips or similar securing structures. In embodiments that include a tissue bolstering material (e.g., a surgical buttress), the tissue bolstering material can be either planar or tubular in configuration. In some embodiments, the implant is a compliant material with a plurality of prepositioned surgical fasteners that facilitate fastening of the implant to a specific anatomic location or tissue. The apparatus can be pre-loaded with a surgical implant. The apparatus includes retainers configured to engage the buttress material and releasably retain the buttress material on the jaws of the apparatus prior to affixation to tissue. In certain embodiments, the retainers remain with the jaws of the instrument after attachment to tissue. In alternative embodiments, the retainers remain with the buttress material after being stapled to tissue. Some embodiments include a system and apparatus to apply a surgical implant of an implantable material or surgical fabric to a resection margin. The implantable material or surgical fabric may be a drug-eluting material used to locally administer one or more drugs.

Some embodiments relate to an introducer for a drug-eluting surgical buttress material and a method of use of such an introducer. In some embodiments, the introducer positions the drug-eluting surgical buttress at or on the site of interest where it is fastened to the site of interest. In some embodiments, the drug-eluting surgical buttress material is secured on or over a surgical resection margin by suturing, clipping, pinning, stapling, gluing, using a hydrogel adhesive, or another suitable attachment technique. Some embodiments also provide a method of applying a surgical buttress or implant material that substantially reduces misalignments of the surgical buttress or implant material at the surgical margin resulting from a user's difficulty in simultaneously aligning, holding in place, and securing the surgical buttress or implant. Some embodiments enable use of a one-step method of applying and securing a surgical buttress or implant material to a surgical resection margin or edge of tissue.

Components of the introducer, cartridge, surgical mesh or implant material, and fixation elements may include any or all of materials that are non-biodegradable, materials that are biodegradable, and materials that are bioerodable materials. For example, in some embodiments, some or all of the components of the introducer may be formed of non-biodegradable and non-bioerodable materials. In some embodiments, some or all of the components of the introducer may be formed of materials that can withstand sterilization for reuse. In some embodiments, only some portions of the introducer are reusable and can withstand sterilization and other portions are single use. As another example, in some embodiments, the surgical mesh or implant material is formed of a biodegradable material that may also be a bioerodable material. In some embodiments, the fixation elements are formed from a biodegradable material that may also be a bioerodable material. In some embodiments, the cartridge may also be formed at least in part of a biodegradable material and/or a bioerodable material.

Some embodiments provide a system for delivery of a surgical mesh or buttress material. The system includes an introducer and a fixed or pivoting attachment cartridge component that can accommodate a surgical mesh or buttress material and can be inserted into a body cavity. The attachment cartridge component may be detachable from the introducer in some embodiments. The system also includes a surgical mesh or buttress material buttress loaded into the head portion of the introducer. The surgical mesh or buttress material may be releasably held in place on the introducer head by one or more mechanical elements or glue points on the surgical mesh or buttress material, on the introducer, or on both. In some embodiments, mechanical elements or glue points that releasably hold the surgical mesh or buttress material in the introducer head may be separate from fixation elements used to affix the surgical mesh or buttress material to the tissue. In some embodiments, some or all of mechanical elements or glue points that releasably hold the surgical mesh or buttress material in the introducer head may aid in affixing the surgical mesh or buttress material to the tissue. The system includes an articulation mechanism configured to articulate the combined cartridge and head relative to an elongate body of the introducer using a handle of the introducer. In some embodiments, the introducer includes both components designed to be reused and single use components.

Surgeons have acknowledged that and studies have shown that laparoscopic techniques require greater concentration and place greater mental and physical stress on surgeons than open surgery. Many tools currently employed in laparoscopic surgery are difficult for surgeons to use, and because of suboptimal design, some tools may actually be doing harm to the highly trained laparoscopic physician. Additionally, poor design of laparoscopic tools increases physician fatigue, creating potential for errors that may harm the patient.

Specialized instruments are required for laparoscopic surgery due to small access ports. The design of these instruments is critical to the result of the surgery. Current laparoscopic instruments have been found to be very poorly designed ergonomically and it is likely that ergonomics were not considered at all. Some practicing laparoscopic surgeons frequently experience post-operation pain or numbness. This is generally attributable to pressure points on the laparoscopic tool handle. Furthermore, four different handle designs used on laparoscopic tools (shank, pistol, axial, and ring handle) have been found to result in either painful pressure spots or to cause extreme ulnar deviation. It would be beneficial to have a laparoscopic tool with an ergonomic handle, an intuitive hand/tool interface, and an articulating end effector. Surgical instrument handles (e.g., the introducer handle) described herein employ a natural gripping mechanism and motion between the wrist and hand of the surgeon for manipulation and use of the handle. In some embodiments, the surgical instrument handle (e.g., the introducer handle) additionally provides a means for locking the handle in a variety of positions.

Example Embodiments

Before explaining at least one embodiment of the invention in detail, it should be understood that the invention is not limited in its application to the details of construction and the arrangements of the components set forth in the following description or illustrated in the drawings. The invention is capable of other embodiments or of being practiced of carried out in various ways. Also, it is to be understood that the phraseology and terminology employed herein is for the purpose of description and should not be regarded as limiting. Embodiments of the present invention, the construction of the embodiments, and methods of using embodiment are described below.

An embodiment includes an implant (e.g., surgical buttress, surgical mesh) delivery system for positioning and affixing an implant (e.g., a surgical buttress, a surgical mesh) covering a surgical margin. As used herein, the term implant refers to one or more layers of material with mechanical properties that allow the implant to cover and be affixed to internal body tissue (e.g., to an internal surgical margin). Examples of an implant include, but are not limited to a surgical buttress and a surgical mesh. One of ordinary skill in the art would recognize that systems, methods and introducers disclosed herein could use any suitable type of implant.

In some embodiments, the implant is a surgical buttress configured for tissue reinforcement. In some embodiments, the implant includes a bioactive agent. In some embodiments, the bioactive agent is incorporated into a coating on a material of the implant (e.g., in a coating on or in a mesh). In some embodiments, the bioactive agent is incorporated into microparticles or nanoparticles within a coating on a material of the implant.

A "bioactive agent" refers to an agent that is capable of exerting a biological effect in vitro and/or in vivo. The biological effect can be therapeutic in nature. As used herein, "bioactive agent" refers also to a substance that is used in connection with an application that is diagnostic in nature, such as in methods for diagnosing the presence or absence of a disease in a patient. The bioactive agents can be neutral or positively or negatively charged. Examples of suitable bioactive agents include pharmaceuticals and drugs, cells, gases and gaseous precursors (e.g., $O_2$), synthetic organic molecules, proteins, enzymes, growth factors, vitamins, steroids, polyanions, nucleosides, nucleotides, polynucleotides, and diagnostic agents, such as contrast agents for use in connection with magnetic resonance imaging, ultrasound, positron emission transmography, computed tomography, or other imaging modality of a patient.

Bioactive agents employed may include therapeutic agents. Bioactive agents that may be employed include chemotherapeutics, antibiotics, antivitals, antiinflammatories, cytokines, targeting compounds, immunotoxins, anti-tumor antibodies, anti-angiogenic agents, anti-edema agents, radiosensitizers, nucleic acids, prodrugs or analogs and combinations thereof.

In some embodiments, the therapeutic agent may be a cancer treating agent. In some embodiments, the cancer treating agent may be chemotherapy agent, which may be one or more of an alkylating agent, and antimetabolite, an anti-microtubule agent, a topoisomerase inhibitor and a cytotoxic antibody.

Any bioactive agent can be incorporated into the implants described herein. For example, a surgical mesh or particle attached to or embedded in a surgical mesh described herein can incorporate a pharmaceutical agent selected from among (1) nonsteroidal anti-inflammatory drugs (NSAIDs) analgesics, such as diclofenac, ibuprofen, ketoprofen, and naproxen; (2) opiate agonist analgesics, such as codeine, fentanyl, hydromophone, and morphine; (3) salicylate analgesics, such as aspirin (ASA) (enteric coated ASA); (4) H1-blocker antihistamines, such as clemastine and terfenadine; (5) H2-blocker antihistamines, such as cimetidine, famotidine, nizadine, and ranitidine; (6) anti-infective agents, such as mupirocin; (7) anti-anaerobic anti-infectives, such as chloramphenicol and clindamycin; (8) antifungal antibiotic anti-infectives, such as amphotericin b, clotrimazole, fluconazole, and ketoconazole; (9) macrolide antibiotic anti-infectives, such as azithromycin and erythromycin; (10) miscellaneous beta-lactam antibiotic anti-infectives, such as aztreonam and imipenem; (11) penicillin antibiotic anti-infectives, such as nafcillin, oxacillin, penicillin G, and penicillin V; (12) quinolone antibiotic anti-infectives, such as ciprofloxacin and norfloxacin; (13) tetracycline antibiotic anti-infectives, such as doxycycline, minocycline, and tetracycline; (14) antituberculosis antimycobacterial anti-infectives such as isoniazid (INH), and rifampin; (15) antiprotozoal anti-infectives, such as atovaquone and dapsone; (16) antimalarial antiprotozoal anti-infectives, such as chloroquine and pyrimethamine; (17) anti-retroviral anti-infectives, such as ritonavir and zidovudine; (18) antiviral anti-infective agents, such as acyclovir, ganciclovir, interferon alpha, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antimetabolite antineoplastic agents, such as fiuorouracil (5-FU) and gemcitabine; (23) hormonal antineoplastics, such as goserelin, leuprolide, and tamoxifen; (24) natural antineoplastics, such as aldesleukin, interleukin-2, docetaxel, etoposide (VP-16), interferon alpha, paclitaxel, and tretinoin (ATRA); (25) antibiotic natural antineoplastics, such as bleomycin, dactinomycin, daunorubicin, doxorubicin, and mitomycin; (26) vinca alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasympathomimetics, such as pilocarpine; (32) cholinesterase inhibitor parasympathomimetics, such as pyridostigmine; (33) alpha-blocker sympatholytics, such as prazosin; (34) beta-blocker sympatholytics, such as atenolol; (35) adrenergic agonist sympathomimetics, such as albuterol and dobutamine; (36) cardiovascular agents, such as aspirin (ASA), plavix (Clopidogrel bisulfate) etc.; (37) beta-blocker antianginals, such as atenolol and propranolol; (38) calcium-channel blocker antianginals, such as nifedipine and verapamil; (39) nitrate antianginals, such as isosorbide dinitrate (ISDN); (40) cardiac glycoside antiarrhythmics, such as digoxin; (41) class I anti-arrhythmics, such as lidocaine, mexiletine, phenytoin, procainamide, and quinidine; (42) class II antiarrhythmics, such as atenolol, metoprolol, propranolol, and timolol; (43) class III antiarrhythmics, such as amiodarone; (44) class IV antiarrhythmics, such as diltiazem and verapamil; (45) alpha-blocker antihypertensives, such as prazosin; (46) angiotensin-converting enzyme inhibitor (ACE inhibitor) antihypertensives, such as captopril and enalapril; (47) beta blocker antihypertensives, such as atenolol, metoprolol, nadolol, and propanolol; (48) calcium-channel blocker antihypertensive agents, such as diltiazem and nifedipine; (49) central-acting adrenergic antihypertensives, such as clonidine and methyldopa; (50) diurectic antihypertensive agents, such as amiloride, furosemide, hydrochlorothiazide (HCTZ), and spironolactone; (51) peripheral vasodilator antihypertensives, such as hydralazine and minoxidil; (52) antilipemics, such as gemfibrozil and probucol; (53) bile acid sequestrant antilipemics, such as cholestyramine; (54) HMG-CoA reductase inhibitor antilipemics, such as lovastatin and pravastatin; (55) inotropes, such as amrinone, dobutamine, and dopamine; (56) cardiac glycoside inotropes, such as digoxin; (57) thrombolytic agents or enzymes, such as alteplase (TPA), anistreplase, streptokinase, and urokinase; (58) dermatological agents, such as colchicine, isotretinoin, methotrexate, minoxidil, tretinoin (ATRA); (59) dermatological corticosteroid anti-inflammatory agents, such as betamethasone and dexamethasone; (60) antifungal topical antiinfectives, such as amphotericin B, clotrimazole, miconazole, and nystatin; (61) antiviral topical anti-infectives, such as acyclovir; (62) topical antineoplastics, such as fluorouracil (5-FU); (63) electrolytic and renal agents, such as lactulose; (64) loop diuretics, such as furosemide; (65) potassium-sparing diuretics, such as triamterene; (66) thiazide diuretics, such as hydrochlorothiazide (HCTZ); (67) uricosuric agents, such as probenecid; (68) enzymes such as RNase and DNase; (69) immunosupressive agents, such as cyclosporin steroids, methotrexate tacrolimus, sirolimus, rapamycin; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) $H_2$-blocker anti-ulcer agents, such as cimetidine, famotidine, nizatidine, and ranitidine; (74) digestants, such as pancrelipase; (75) prokinetic agents, such as erythromycin; (76) opiate agonist intravenous anesthetics such as fentanyl; (77) hematopoietic antianemia agents, such as erythropoietin, filgrastim (G-CSF), and sargramostim (GM-CSF); (78) coagulation agents, such as antihemophilic factors 1-10 (XHF 1-10); (79) anticoagulants, such as warfarin, heparin, and argatroban; (80) growth receptor inhibitors, such as erlotinib and gefetinib; (82) abortifacients, such as methotrexate; (83) antidiabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadatropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-1b and interferon gamma-1b; (93) immunoglobulins, such as immune globulin IM, IMIG, IGIM and immune globulin IV, IVIG, IGIV; (94) amide local anesthetics, such as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs (NSAIDs), such as diclofenac, ibuprofen, ketoprofen, ketorlac, and naproxen; (99) skeletal muscle relaxants, such as baclofen, cyclobenzaprine, and diazepam; (100) reverse neuromuscular blocker skeletal muscle relaxants, such as pyridostigmine; (101) neurological agents, such as nimodipine, riluzole, tacrine and ticlopidine; (102) anticonvulsants, such as carbamazepine, gabapentin, lamotrigine, phenytoin, and valproic acid; (103) barbiturate anticonvulsants, such as phenobarbital and primidone; (104) benzodiazepine anticonvulsants, such as clonazepam, diazepam, and lorazepam; (105) anti-parkisonian agents, such as bromocriptine, levodopa, carbidopa, and pergolide; (106) anti-vertigo agents, such as meclizine; (107) opiate agonists, such as codeine, fentanyl, hydromorphone, methadone, and morphine; (108) opiate antagonists, such as naloxone; (109) beta-blocker anti-glaucoma agents, such as timolol; (110) miotic anti-glaucoma agents, such as pilocarpine; (111) ophthalmic aminoglycoside antiinfectives, such as gentamicin, neomycin, and tobramycin; (112) ophthalmic quinolone anti-infectives, such as ciprofloxacin, norfloxacin, and ofloxacin; (113) ophthalmic corticosteroid anti-inflammatory agents, such as dexamethasone and prednisolone; (114) ophthalmic nonsteroidal anti-inflammatory drugs (NSAIDs), such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psychostimulants, such as methylphenidate and pemoline; (118) antitussives, such as codeine; (119) bronchodilators, such as theophylline; (120) adrenergic agonist bronchodilators, such as albuterol; (121) respiratory corticosteroid anti-inflammatory agents, such as dexamethasone; (122) antidotes, such as flumazenil and naloxone; (123) heavy metal antagonists/chelating agents, such as penicillamine; (124) deterrent substance abuse agents, such as disulfiram, naltrexone, and nicotine; (125) withdrawal substance abuse agents, such as bromocriptine; (126) minerals, such as iron, calcium, and magnesium; (127) vitamin B compounds, such as cyanocobalamin (vitamin B12) and niacin (vitamin B3); (128) vitamin C compounds, such as ascorbic acid; (129) vitamin D compounds, such as calcitriol; (130) vitamin A, vitamin E, and vitamin E compounds; (131) poisons, such as racin; (132) anti-bleeding agents, such as protamine; (133) antihelminth anti-infectives, such as metronidazole; and (134) sclerosants such as talc, alcohol, and doxycyclin.

In addition to the foregoing, the following less common drugs can also be used: chlorhexidine; estradiol cypionate in oil; estradiol valerate in oil; flurbiprofen; flurbiprofen sodium; ivermectin; levodopa; nafarelin; and somatropin. Further, the following drugs can also be used: recombinant beta-glucan; bovine immunoglobulin concentrate; bovine superoxide dismutase; the formulation comprising fluorouracil, epinephrine, and bovine collagen; recombinant hirudin (r-Hir), HIV-I immunogen; human anti-TAC antibody; recombinant human growth hormone (r-hGH); recombinant human hemoglobin (r-Hb); recombinant human mecasermin (r-IGF-1); recombinant interferon beta-Ia; lenograstim (G-CSF); olanzapine; recombinant thyroid stimulating hormone (r-TSH); and topotecan. Further still, the following intravenous products can be used: acyclovir sodium; aldesleukin; atenolol; bleomycin sulfate, human calcitonin; salmon calcitonin; carboplatin; carmustine; dactinomycin, daunorubicin HCl; docetaxel; doxorubicin HCl; epoetin alpha; etoposide (VP-16); fluorouracil (5-FU); ganciclovir sodium; gentamicin sulfate; interferon alpha; leuprolide acetate; meperidine HCl; methadone HCl; methotrexate sodium; paclitaxel; ranitidine HCl; vinblastin sulfate; and zidovudine (AZT). Further specific examples of useful pharmaceutical agents from the above categories include: (a) anti-neoplasties such as androgen inhibitors, antimetabolites, cytotoxic agents, receptor inhibitors, and immuno-modulators; (b) anti-tussives such as dextromethorphan, dextromethorphan hydrobromide, noscapine, carbetapentane citrate, and chlorphedianol hydrochloride; (c) antihistamines such as chlorpheniramine maleate, phenindamine tartrate, pyrilamine maleate, doxyl amine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, .codeine sulfate and morphine; (f) mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (j) appetite suppressants such as phenylpropanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines, and other bioactive peptidic compounds, such as interleukins 1-18 including mutants and analogues, RNase, DNase, luteinizing hormone releasing hormone (LHRH) and analogues, gonadotropin releasing hormone (GnRH), transforming growth factor-β. (TGF-beta), fibroblast growth factor (FGF), tumor necrosis factor-alpha & beta (TNF-alpha & beta), nerve growth factor (NGF), growth hormone releasing factor (GHRF), epidermal growth factor (EGF), fibroblast growth factor homologous factor (FGFHF), hepatocyte growth factor (HGF), insulin growth factor (IGF), invasion inhibiting factor-2 (IIF-2), bone morphogenetic proteins 1-7 (BMP 1-7), somatostatin, thymosin-alpha-1, gamma-globulin, superoxide dismutase (SOD), complement factors, hGH, tPA, calcitonin, ANF, EPO and insulin; (n) anti-infective agents such as antifungals, antivirals, antihelminths, antiseptics and antibiotics; and (m) oxygen, hemoglobin, nitric or sliver oxide.

Non-limiting examples of broad categories of useful pharmaceutical agents include the following therapeutic categories: anabolic agents, anesthetic agents, antacids, anti-asthmatic agents, anticholesterolemic and anti-lipid agents, anti-coagulants, anticonvulsants, anti-diarrheals, antiemetics, anti-infective agents, anti-inflammatory agents, anti-manic agents, anti-nauseants, antineoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and antithyroid agents, uterine relaxants, vitamins, and prodrugs.

Examples of specific drugs that can be used include: asparaginase, bleomycin, busulfan, capecitabine, carboplatin, carmustine, chlorambucil, cisplatin, cyclophosphamide, cytarabine, dacarbizine, dactinomycin, daunorubicin, dexrazoxane, docetaxel, doxorubicin, etoposide, fioxuridine, fludarabine, fluoruracil, gemcitabine, hydroxyurea, idarubicin, ifosfamide, irinotecan, lomustine, mechlorethamine, melphalan, mercaptopurine, methotrexate, mitomycin, mitotane, mitoxantrone, paclitaxel, pentostatin, plicamycin, pre-mextred procarbazine, rituximabe, streptozocin, teniposid, thioguanine, thiotepa, vinplastine, vinchristine, and vinorelbine. In some embodiments, the drugs for lung cancer treatment is paclitaxel, pemetrexed, 10-hydrocamptothecin, irinotecan, erlotinibil/gefetinib or derivates of these molecules.

Examples of anticancer, antineoplastic agents are camp-tothecins. These drugs are antineoplastic by virtue of their ability to inhibit topoisomerase I. Camptothecin is a plant alkaloid isolated from trees indigenous to China and analogs thereof such as 9-aminocamptothecin, 9-nitrocamptothecin, 10-hydroxycamptothecin, 10,11-methylenedioxycamptothecin, 9-m'tro-10,11-methylenehydroxycamptothecin, 9-chloro-10, 11-methylenehydroxycamptothecin, 9-amino-10,11-methylenehydroxycamptothecin, 7-ethyl-1O-hydroxycamptothecin (SN-38), topotecan, DX-8951, Lurtotecan (GII147221C), and other analogs (collectively referred to herein as camptothecin drugs) are presently under study worldwide in research laboratories for treatment of colon, breast, and other cancers.

Additionally, the pharmaceutical agent can be a radiosensitizer, such as metoclopramide, sensamide or neusensamide (manufactured by Oxigene); profiromycin (made by Vion); RSR13 (made by Allos); THYMITAQ® (made by Agouron), etanidazole or lobenguane (manufactured by Nycomed); gadolinium texaphrin (made by Pharmacyclics); BuDR/Broxine (made by NeoPharm); EPdR (made by Sparta); CR2412 (made by Cell Therapeutic); L1X (made by Terrapin); agents that minimize hypoxia, and the like.

The bioactive agent can be selected from a biologically active substance. The biologically active substance can be selected from the group consisting of peptides, poly-peptides, proteins, amino acids, polysaccharides, growth factors, hormones, anti-angiogenesis factors, interferons or cytokines, elements, and pro-drugs. In useful embodiments, the biologically active substance is a therapeutic drug or pro-drug, in some embodiments, a drug selected from the group consisting of chemotherapeutic agents and other antineoplastics such as paclitaxel, antibiotics, anti-virals, antifungals, anesthetics, antihelminths, antiinflammatories, and anticoagulants. In certain useful embodiments, the therapeutic drug or pro-drug is selected from the group consisting of chemotherapeutic agents and other antineoplastics such as paclitaxel, carboplatin and cisplatin; nitrosourea alkylating antineoplastic agents, such as carmustine (BCNU); fluorouracil (5-FU) and gemcitabine; hormonal antineoplastics, such as goserelin, leuprolide, and tamoxifen; receptor inhibitors such as erlotinib, gefetinib, sutent or anti-ckit inhibitors, such as GLEEVEC®; natural antineoplastics, such as aldesleukin, interleukin-2, docetaxel, etoposide (VP-16), interferon alpha, paclitaxel, and tretinoin (ATRA).

In another embodiment, the biologically active substance is a nucleic acid sequence. The nucleic acid sequence can be selected from among any DNA or RNA sequence. In certain embodiments, the biologically active substance is a DNA sequence that encodes a genetic marker selected from among luciferase gene, β-galactosidase gene, resistance, neomycin resistance, and chloramphenicol acetyl transferase. In certain embodiments, the biologically active substance is a DNA sequence that encodes a lectin, a mannose receptor, a sialoadhesin, or a retroviral transactivating factor. In certain embodiments, the biologically active substance is a DNA sequence that encodes a RNA selected from the group consisting of a sense RNA, an antisense RNA, siRNA and a ribozyme.

Biologically active agents amenable for use with surgical meshes described herein include, without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment. Useful active agents amenable for use in the new compositions include growth factors, such as transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins, are preferred. Members of the TGF supergene family include the beta-transforming growth factors (for example, TGF-b1, TGF-b2, and TGF-b3); bone morphogenetic proteins (for example, BMP-I, BMP-2, BMP-3, BMP-4, BMP-5, BMP-6, BMP-7, BMP-8, and BMP-9); heparin-binding growth factors (for example, fibroblast growth factor (FGF), epidermal growth factor (EGF), platelet-derived growth factor (PDGF), and insulin-like growth factor (IGF)); inhibins (for example, Inhibin A, Inhibin B); growth differentiating factors (for example, GDF-1); and activins (for example, Activin A, Activin B, and Activin AB), In some embodiments, each of the bioactive agents is independently selected from the group consisting of an antibiotic, an antimitotic, an anti-inflammatory agent, a growth factor, a targeting compound, a cytokine, an immunotoxin, an anti-tumor antibody, an anti-angiogenic agent, an anti-edema agent, a radiosensitizer, and a chemotherapeutic. In some embodiments, at least one of the one or more independently selected bioactive agents is camptothecin. In some embodiments, at least one of the one or more independently selected bioactive agents is 10-hydroxycamptothecin. In some embodiments, at least one of the one or more independently selected bioactive agents is paclitaxel. In some embodiments, at least one of the one or more independently selected bioactive agents is a platinum containing molecule: In some embodiments, the platinum containing molecule is selected from the group consisting of cisplatin and carboplatinum. In some embodiments, at least one of the one or more independently selected bioactive agents is a chemotherapeutic agent.

In some embodiments, the implant may be configured to support cellular ingrowth for tissue repair and restoration. The implant may include a bioactive agent for promoting cellular ingrowth (e.g., one or more growth factors).

In some embodiments, the implant (e.g., surgical mesh and/or plurality of associate fixation element or clamp) include a visualization agent (e.g., gadolinium chelate, silver, iron oxide, magnesium, copper manganese, barium, tantalum, technetium, dye pigment or colorant, etc.).

Films that may be employed as a surgical mesh and particles that may be included in the surgical mesh of some embodiments are described in U.S. Pat. No. 7,671,095 to Colson et al., which is incorporated herein by reference in its entirety.

FIG. 1 schematically depicts a system 10 including an introducer 12 and a cartridge 14, in accordance with an embodiment. The cartridge 14 releasably holds a surgical mesh 20 and a plurality of fixation elements 30 associated with the surgical mesh. The surgical mesh 20 has a first surface 22, a first end portion 24, and a second end portion 26. FIG. 1 shows the surgical mesh 20 separate from the cartridge 14 for illustrative purposes. The cartridge 14 positions the first surface 22 at the first end portion 24 of the surgical mesh facing, and separated from, the first surface 22 at the second end portion 26 of the surgical mesh by a gap G. The fixation elements 30 are positioned at the first end portion 24 and/or at the second end portion 26 of the surgical mesh 30. As depicted in FIG. 1, the fixation elements 30 are positioned at the first end portion 26 and the second end portion 26 of the surgical mesh 30.

In some embodiments, the fixation elements are biodegradable fixation elements. In some embodiments, the fixation elements are bioabsorbable fixation elements.

In some embodiments, the fixation elements 30 are attached to the surgical mesh 30 before the surgical mesh is affixed to the surgical margin. In some embodiments, the fixation elements are releaseably attached to the cartridge before affixing the surgical mesh to the surgical margin. For example, the fixation elements may be releasably attached to the cartridge using one or more of spaced barbs, sutures, tacks, clips and tack welds.

In some embodiments, the fixation elements are attached to the surgical mesh prior to actuation of the introducer. In some embodiments, the fixation elements are attached to the surgical mesh through the actuation of the introducer In some embodiments, the fixation elements for affixing the surgical mesh to the tissue include one or more of surgical sutures, clips, tacks, and tissue anchors.

The introducer 12 includes an elongate body 32 having a proximal end portion 34 and a distal end portion 36. The introducer 12 also includes a head 40 pivotably coupled to the distal end portion 36 of the elongate body and configured to receive the cartridge 14 forming a combined head and cartridge. The combined head and cartridge is configured to receive a surgical margin (not shown) in the gap G, and configured to position the first surface 22 of the surgical mesh covering the surgical margin (not shown). The introducer 12 also includes a handle 42 connected with the proximal end portion 34 of the elongate body. The handle 42 includes a grip 43 and an in-line trigger 46, an articulation mechanism 48 and an actuation mechanism. The articulation mechanism is configured to articulate the combined cartridge and head relative to the elongate body 32 using the handle 42. The actuation mechanism is configured to affix the surgical mesh 20 to the surgical margin using the one or more fixation elements 30.

The combined cartridge and head may include curved jaws 44, 46 for holding the surgical mesh 20 which are connected by a hinge 48. The curved jaws may include registration points for registration of points on the surgical mesh with corresponding points on the jaws. In some embodiments, the surgical mesh is releasably attached to the jaws at the registration points 50a-50i (e.g., using pins, adhesive, weld points).

FIG. 2 schematically depicts an alternative embodiment of the system in which the combined cartridge and head includes planar jaws 44', 46' for holding a surgical mesh 20'.

FIG. 3 schematically depicts the distal end portion 36 of the elongate body and the combined head 40 and cartridge 14 holding the surgical mesh 20 with the registration points 50a-50i.

Figure 4:
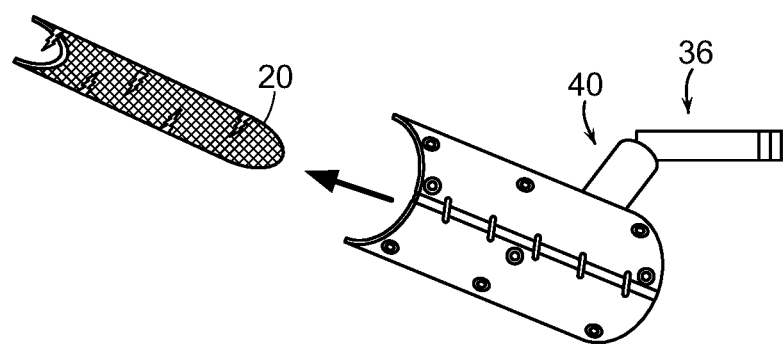
FIG. 4 schematically depicts the head and distal portion of the apparatus of FIG. 3 after the surgical mesh is released from the head.

FIG. 4 schematically depicts the distal end portion 36 of the elongate body and the combined head 40 and cartridge 14 after actuation and release of the surgical mesh 20 from the introducer (the tissue to which the surgical mesh has been attached is not shown).

Figure 5:
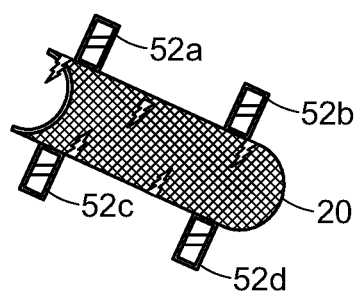
FIG. 5 schematically depicts a surgical mesh including a plurality of fixation elements and a plurality of tabs, in accordance with an embodiment.

In some embodiments, the surgical mesh may include structural features for releasably securing the surgical mesh to the combined head and cartridge. FIG. 5 schematically depicts a mesh 20 including tabs 52a-52d for releasably securing the surgical mesh 20 to the combined cartridge and head. For example, in some embodiments, each tab includes one or more apertures (not shown) and the combined head and cartridge includes one or more protrusions (not shown) that extend through the corresponding one or more apertures to secure the surgical mesh to the combined cartridge and head. In some embodiments, each tab is connected with a body of the surgical mesh by a region of reduced strength (e.g., a perforation) that allows a body of the surgical mesh to be torn away from the tabs. In some embodiments, the tabs remain connected with a body of the surgical mesh after the surgical mesh is attached to tissue.

Figure 6:
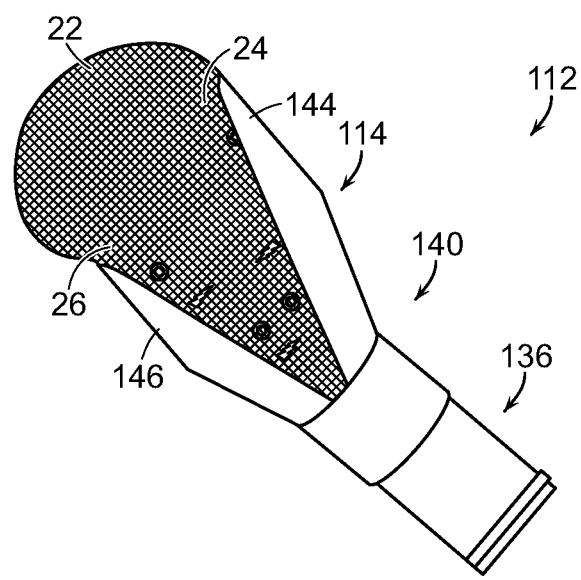
FIG. 6 schematically depicts a head and distal portion of an elongate body of an introducer showing a combined head and cartridge having an in line configuration with respect to a longitudinal axis of the elongate body, in accordance with an embodiment.

FIG. 6 schematically depicts an embodiment of an introducer 112 in which jaws 144, 146 of a combined head 140 and cartridge 114 are substantially in-line with a distal end portion 136 of the elongate body.

Figure 7:
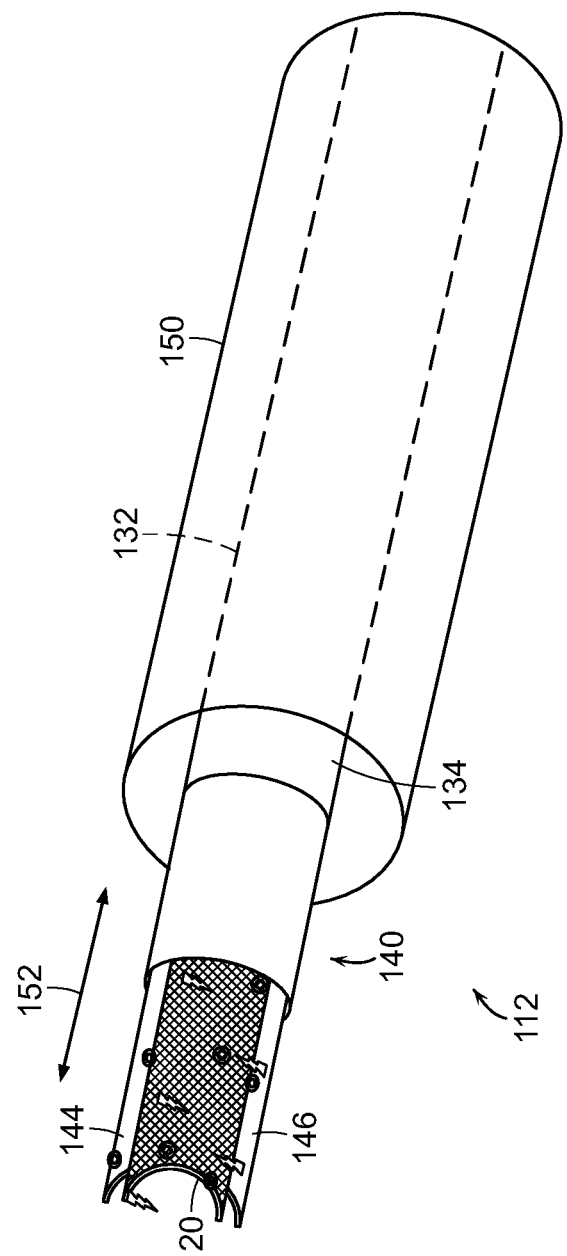
FIG. 7 schematically depicts a combined head and cartridge being extended from a distal end of an introducer shaft, in accordance with some embodiments.

In some embodiments, the introducer includes a shaft through which the head is extended. FIG. 7 schematically depicts the combined head 140 and cartridge 114 and distal end portion 136 of an elongate body 132 extending from a distal end of the shaft 150, in accordance with an embodiment. As illustrated by arrow 152, the combined head 140 and cartridge 114 can be extended from the shaft 150 (e.g., to be deployed) or withdrawn into the shaft 150.

Figure 8:
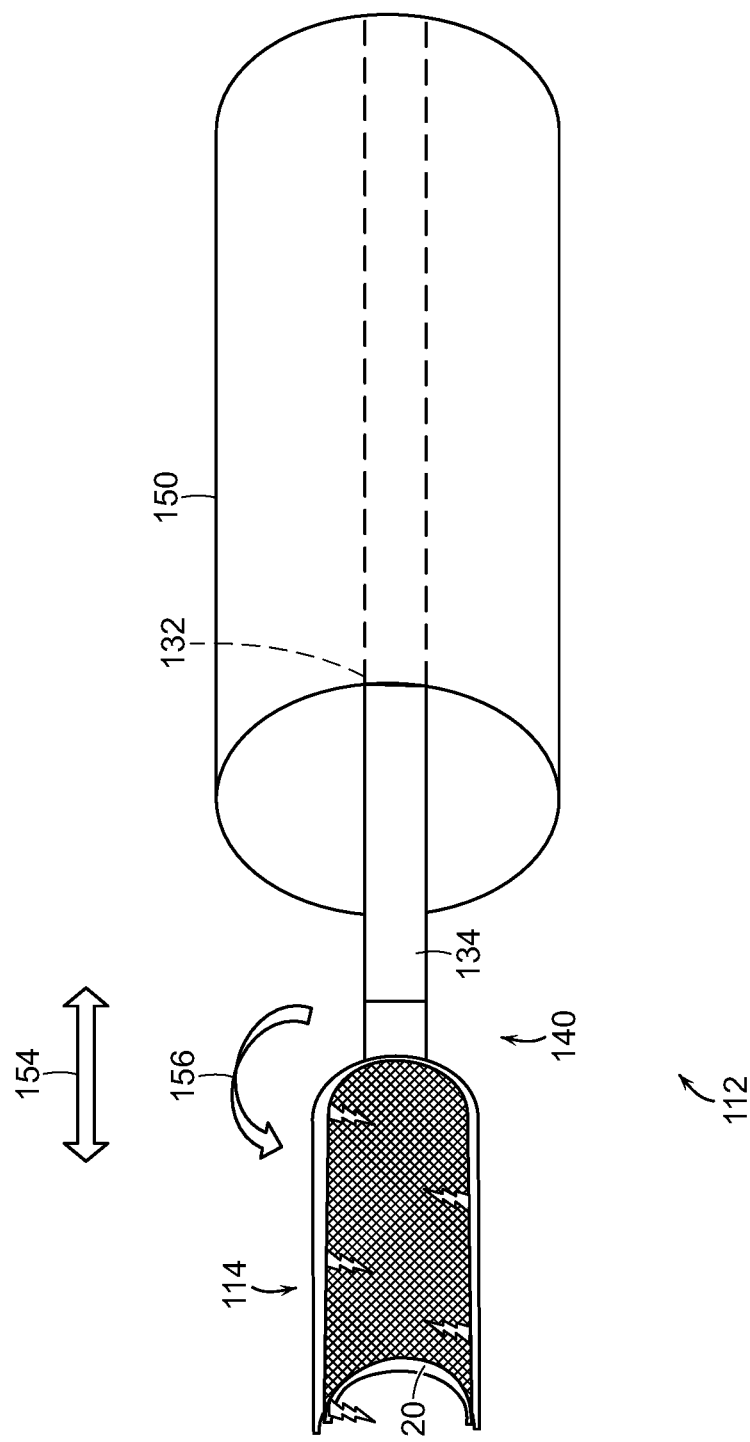
FIG. 8 schematically depicts a combined head and cartridge extending from a distal end of an introducer shaft illustrating angular articulation, in accordance with some embodiments.

FIG. 8 schematically depicts the combined head 140 and cartridge 114 extended and deployed from the shaft 150. As illustrated by arrow 154, cartridge 114 may be advanced by and withdrawn with respect to the shaft 150. As illustrated by arrow 156, cartridge 114 may be angularly articulated relative to the shaft 150.

Figure 9:
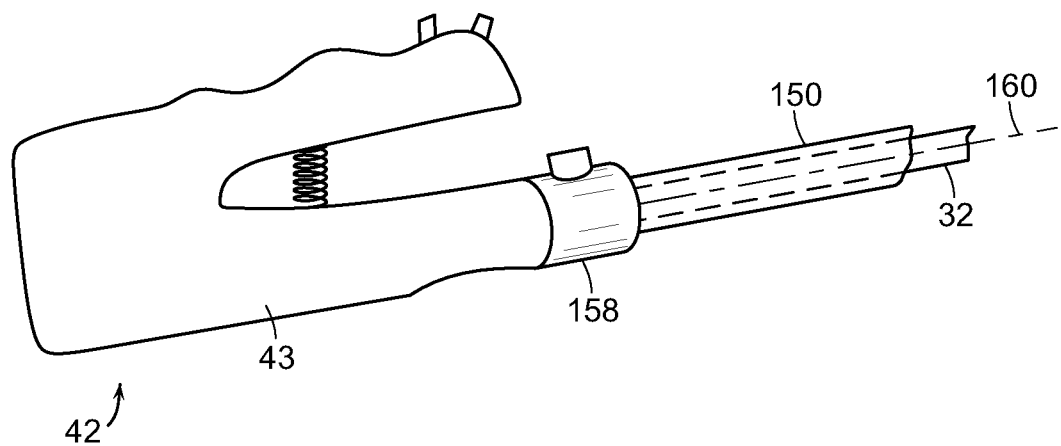
FIG. 9 schematically depicts an in-line handle of an introducer with articulation controls, in accordance with some embodiments.

FIG. 9 schematically depicts an in-line handle 42 connected with a proximal end portion of the elongate body 32. The handle 32 may include a mechanism (e.g., a collet 158) for rotating the elongate body 32 about longitudinal axis 160 of the elongate body relative to the handle 42. The handle may include a lock for locking an angular orientation of the elongate body 32 relative to an orientation of the handle 42. The handle may also include an ergonomic grip 43.

Figure 10:
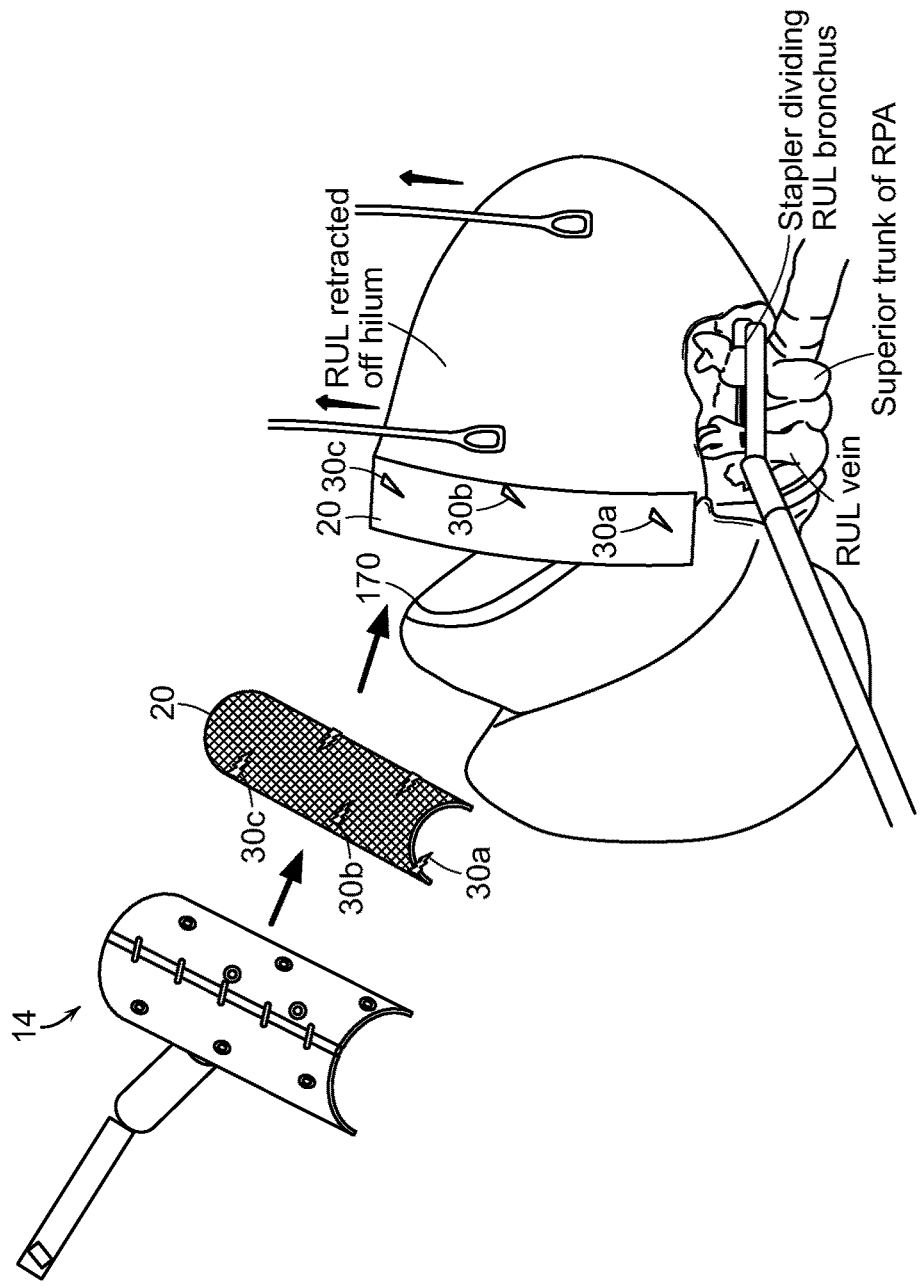
FIG. 10 schematically depicts positioning and affixing a surgical material over a resection line, in accordance with some embodiments.

FIG. 10 schematically depicts positioning and affixing a surgical material 20 over a resection line 170 using an introducer, in accordance with some embodiments.

Figure 11:
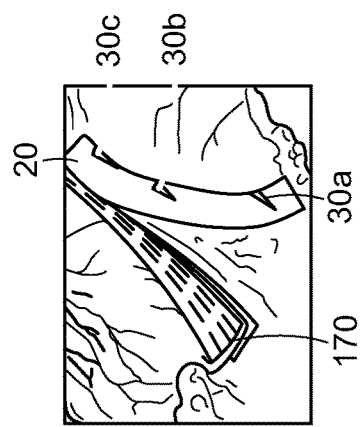
FIG. 11 schematically depicts a surgical material affixed to a resection line, in accordance with some embodiments.

FIG. 11 schematically depicts the surgical material 20 affixed to and covering the resection line 170.

Some embodiments of the surgical apparatus described herein includes a first jaw structure configured and dimensioned for housing a plurality of surgical fasteners, a second jaw structure configured and dimensioned for effecting closure of a plurality of fasteners and at least one biocompatible surgical fabric operatively associated with either or both of the first and second jaw structures, wherein at least a portion of the fabric is disposed between the first and second jaw structures. Both the anvil portion and the fastener ejecting portion of the device are at least partially covered with the implant or bolstering material. In use, tissue is disposed between the anvil portion and the fixation portion of the instrument and the instrument is fired. The implant material or bolstering material is thereby secured to the tissue and releasably detaches from the device upon withdrawal of the device from the surgical site. The specific design or type of surgical apparatus employed in carrying out this invention is not critical so long as the basic structural elements are present. The apparatus can be one that is particularly suited for open surgery or, alternatively, for laparoscopic and/or endoscopic surgery.

Additional embodiments of the presently disclosed surgical implant positioner and apparatus are described below.

Example Embodiment 1

An example embodiment is a surgical apparatus including a device with a handle including a grip (e.g. pistol grip, in line handle, or other ergonomic grip, etc.) used to implant a material which may include a plurality of fasteners and a tissue contacting surface. The distal end of the device, which may be a cartridge unit, is configured to be manipulated by the clinician by articulating the distal end to a desired angle of between 0 degrees relative to the shaft up to 90 degrees relative to the shaft in order to better and more safely navigate through the body and intercept the target tissue or anatomic site.

The handle has a body portion, a top surface, a bottom surface opposite the top surface, a proximal end and distal end, the top surface of the handle being contoured to complement the natural curve of the palm. A shaft projects from the distal end of the handle, the shaft having a proximal and a distal end. The apparatus includes an articulating end effector located at the distal end of the shaft. The end effector comprises graspers or a housing for a surgical implant attached thereto. Attachment elements are associated with the surgical implant. Various mechanical and/or chemical attachment means suitable for attaching the surgical implant to tissue are within the purview of those skilled in the art and include, for example, the use of adhesives, sealants, glues, pins, tacks, tabs, clamps, channels, straps, protrusions, and combinations thereof.

The handle includes a collet rotatable about a longitudinal axis of the shaft. Rotation of the collet drives rotation of the shaft relative to the handle. The handle also includes a squeeze grip lever extending from the bottom surface of the handle that actuates an elongate rod in the shaft to open and close and actuate the device.

The apparatus also includes a control movably mounted to the handle opposite of the shaft. The control (e.g., a control sphere) is rotatable about a first axis to provide a first degree of freedom relative to the handle and to adjust a pitch orientation of the end effector, and wherein the control is rotatable about a second axis to provide a second degree of freedom relative to the handle and adjust a yaw orientation of the end effector. The pitch of the tool is moved upward when the control is moved upward, the pitch of the tool is moved downward when the control is moved downward, the yaw of the tool is moved right when the control is moved right, and the yaw of the tool is moved left when the control is moved left. The control and the end effector rotate with the shaft relative to the handle. All controls on the apparatus can be locked and unlocked as the needs of the clinician dictate.

Example Embodiment 2

According to another aspect of the present disclosure, a surgical apparatus including an in-line handle and a releasable, disposable cartridge assembly is provided. The cartridge assembly is configured to house a releasable implant material including a plurality of fasteners and a tissue contacting surface. A disposable loading unit of this embodiment of the present invention is a replaceable unit which includes an actuating assembly consisting of a pusher assembly having a thrust knob, cam bars and, optionally, knife blade. The disposable loading unit further includes stationary carrier for holding cartridge assembly.

Example Embodiment 3

In some embodiments, an implant material may include a plurality of welds positioned at least partially over retaining slots of a cartridge assembly or housing to hold the implant material in the cartridge or unitary housing.

Example Embodiment 4

In some embodiments, a cartridge assembly is associated with a first jaw of an introducer head and an anvil assembly is associated with a second jaw of an introducer head. The first and second jaws are selectively movable relative to one another from a first spaced apart position to a second position wherein the first and second jaws cooperate to grasp tissue there between. In such embodiments, fixation element retaining slots may linearly extend along a length of the cartridge assembly or the anvil assembly, or on both.

An implant or buttress material of the cartridge assembly may include a plurality of welds overlying at least one row of the fixation element retaining slots of the cartridge assembly to releasably affix the implant material to the cartridge assembly.

Example Embodiment 5

In some embodiments, a cartridge assembly may be associated with a body portion of a surgical fastening apparatus and an anvil assembly includes a shaft removably mountable to the body portion, the anvil assembly being movable toward and away from the body portion. In such embodiments, a buttress material may include a plurality of welds in an annular configuration. The cartridge assembly and the anvil assembly may also include at least two rows of fixation element retaining slots and pockets. The buttress material of the cartridge assembly may include a plurality of welds overlying at least one row of the fixation element retaining slots of the cartridge assembly.

Example Embodiment 6

In some embodiments, a surgical apparatus includes a first jaw structure having a finger-like projection for holding an actuating assembly. The apparatus also includes a second jaw structure including a pair of hinge plates for hingedly connecting to first jaw structure and a finger-like projection for carrying an anvil assembly. The anvil assembly is formed of a plate that may exert a force on fastening elements during actuation. The anvil assembly can include means for holding rows of retainer portions of a two-part surgical fastener.

Example Embodiment 7

In an example embodiment, an apparatus comprises a first jaw structure for holding a cartridge assembly. The cartridge assembly carries a plurality of rows of fixation devices which, upon actuation of the apparatus, substantially simultaneously strike an anvil assembly on a second structure of the apparatus to effect closure.

Example Embodiment 8

In an example embodiment, a biocompatible surgical fabric or implant material is partially or completely disposed between an anvil assembly and a cartridge assembly. The fabric or implant material can be shaped to any desired configuration. The fabric or implant material can have a planar, semitubular, or tubular shape. For fabric or implant material having a planar shape, the implant can be shaped to correspond substantially in size with the tissue contacting surface dimensions of either anvil assembly, cartridge assembly, or be wider than one or both.

Example Embodiment 9

In some embodiments, one or more individual pieces or segments of biocompatible surgical fabric can be employed in carrying out the present invention. Therefore, it is contemplated that two or more pieces or layers of fabric can be attached to a surgical device as herein disclosed. For example, in some embodiments, tubular fabric prosthesis is fitted over an anvil portion and a planar fabric prosthesis is attached to a cartridge assembly. In such a case, body tissue is sandwiched between and secured to both prostheses, thereby providing fabric at both the entry and exit points of the fastening elements. The tubular prosthesis can be subsequently cut longitudinally along its longest axis to provide free ends which can be affixed to surrounding tissue and/or organs for further structural support or localized drug delivery. The surgical implant or fabric can be releasably attached to either anvil assembly or cartridge assembly. Alternatively, the anvil assembly and cartridge assembly can both have fabric disposed thereon in any combination of tubular and planar structure, to provide a tissue/fabric "sandwich" upon actuation of the instrument.

The attachment of the implant or fabric to a surgical device in accordance with this embodiments described herein should be secure enough to prevent the implant or fabric from slipping off the device, yet not be so strong as to inhibit separation of the implant or fabric from the device after the device has been actuated. Such releasable attachment can advantageously be effected by employing a plurality of pins. Clips may also, or alternatively, be employed as the securing means. A combination of pins and/or clips can also be employed. The precise number and location of pins and/or clips is not critical so long as the surgical fabric is releasably attached to the apparatus.

A fabric prosthesis can act as an adhesion barrier, hemostatic agent, reinforcement, tissue growth enhancer, and the like. Furthermore, it shall be understood that fabric prosthesis can have incorporated therein and/or thereon one or more medically and/or surgically useful substances such as drugs, enzymes, growth factors, peptides, proteins, dyes, diagnostic agents or hemostasis agents.

Example Embodiment 10

The apparatus includes a handle having a body portion, a top surface, an opposite bottom surface, a proximal end, and distal end. The top surface of the handle is contoured to compliment the natural curve of the palm. The apparatus further includes a shaft projecting from the distal end of the handle. The shaft has a proximal and distal end. A control sphere is located on the handle. The control sphere can be moved by one or more of a user's fingers or thumb to indicate direction. An end effector is located at the distal end of the shaft. The end effector is connected to the control sphere such that movements made to the control sphere control cause movement (articulation) of the end effector.

Construction of Embodiments

The material of any part of the device may be the same as or different from the material of the implant material, cartridge or assembly. The device and assembly may be fabricated from any material known to those normally skilled in the art. Materials used to fabricate the assembly can include any one or a combination of materials including but not limited to: metals (e.g. titanium, aluminum, steel, magnesium and various alloys like Nitinol, etc.), plastics (e.g., polypropylene, polyethylene, polystyrene, acrylic, nylon, polybenzimidazole, polyvinylchloride, polyvinylalcohol, polytetrafluoroethylene like TEFLON), silicone rubber, polymerized plastics like polyester and epoxies, hybrid materials like fiberglass and carbon fiber hardened with epoxy, polyester resins, or hydrogels.

Biocompatible surgical fabric can be biologically based materials including but not limited to hyaluronic acid, agarose, silk fobroin, self-assembling peptides, polysaccharidic materials, like chitosan, glycosaminoglycans, acellular dermal graft (ALLODERM), acellular collagen (PERISTRIPS) woven, knit or nonwoven and can be bioabsorbable or nonbioabsorbable. Nonwoven bioabsorbable materials are generally preferred in carrying out this invention. Bioabsorbable surgical materials include those fabricated from homopolymers, copolymers or blends obtained from one or more monomers selected from the group consisting of glycolide, glycolic acid, lactide, lactic acid, p-dioxanone, α-caprolactone and trimethylene carbonate. include, but are not limited to, poly(lactic acid), poly(glycolic acid), poly (hydroxybutyrate), poly(phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly (amino acids), copoly(ether-esters), polyalkylene oxalates, polyamides, poly(iminocarbonates), polyalkylene oxalates, polyoxaesters, polyorthoesters, polyphosphazenes and copolymers, block copolymers, homopolymers, blends, and combinations thereof.

In some embodiments, natural biological polymers are used in forming a non-porous and/or porous layer of the surgical buttress. Suitable natural biological polymers include, but are not limited to, collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethyl cellulose, chitan, chitosan, and combinations thereof. In addition, the natural biological polymers may be combined with any of the other polymeric materials described herein to produce a non-porous layer of the surgical implant, fabric or buttress.

Bioabsorbable surgical fabrics, especially those that are nonwoven, manufactured from copolymers of glycolide and lactide may be employed. U.S. Pat. Nos. 3,875,937, 3,937, 223 and 4,128,612, the contents of which are incorporated herein by reference, describe bioabsorbable surgical fabrics suitable for use with some embodiments. Nonbioabsorbable surgical fabrics include those that are fabricated from such polymers as polyethylene, polypropylene, nylon, polyethylene terephthalate, polytetrafluoroethylene, polyvinylidene fluoride, and the like.

Biocompatible implant materials can be fabricated with coatings of various materials. These coatings can be comprised from any useful combination of materials used to cover the base layer. The top layer may be one layer or multiple layers designed to improve the material, functional, or other characteristics of the implant's performance for its intended use. These features include, support for structural integrity of the implant, attachment of implant to assembly or target tissue, lubricity, enhanced flexibility/resilience, resistance or acceleration of degradation, prevention of adverse biologic response to implant (e.g., thrombosis, adhesions, foreign body reaction, etc.) and drug release.

Some non-limiting examples of materials from which non porous and/or porous layers of surgical implant may be made include, but are not limited to, poly(lactic acid), poly(glycolic acid), poly(hydroxybutyrate), poly(phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes and copolymers, block copolymers, homopolymers, blends, and combinations thereof. In some embodiments, natural biological polymers are used in forming a non-porous and/or porous layer of the surgical buttress. Suitable natural biological polymers include, but are not limited to, collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethyl cellulose, chitan, chitosan, and combinations thereof. In addition, the natural biological polymers may be combined with any of the other polymeric materials described herein to produce a non-porous layer of the surgical implant, fabric or buttress.

In some embodiments, amorphous polymers, e.g., thermoplastics, are utilized to form the surgical implant or buttress of the present disclosure. Amorphous polymers melt gradually over a range of temperatures and include, for example, acrylonitrile-butadiene-styrene, acrylic, butadiene-styrene, polycarbonate, polyetherimide, polythalamide, polystyrene, polysulfone, polyvinyl chloride, and styrene-acrylonitrile copolymer.

In embodiments, semi-crystalline materials such as nylon, polyethylene, and polypropylene, may be utilized alone or in combination with other materials to form a surgical implant or buttress. The use of non-porous layer(s) in the surgical implant or buttress may enhance the ability of the surgical implant or buttress to resist tears and perforations during the manufacturing, shipping, handling, and affixing processes. Also, the use of a non-porous layer in the surgical implant or buttress may retard or prevent tissue ingrowth from surrounding tissues thereby acting as an adhesion barrier and preventing the formation of unwanted scar tissue. Thus, in embodiments, the non-porous layer(s) of the surgical implant or buttress may possess anti-adhesion properties. In some embodiment, a non-porous layer may be used to directionally deliver drug toward or away from the tissue to which the implant is affixed. A non-porous layer of the surgical implant may be formed using techniques within the purview of those skilled in the art, such as casting, molding, and the like. Any of the porous layers of the surgical implant or buttress may have openings or pores over at least a portion of a surface thereof.

As described in more detail below, suitable materials for forming a porous layer include, but are not limited to, fibrous structures (e.g., knitted structures, woven structures, non-woven structures, etc.) and/or foams (e.g., open or closed cell foams). In some embodiments, the pores may be in sufficient number and size so as to interconnect across the entire thickness of the porous layer. Woven fabrics, knitted fabrics, and open cell foam are illustrative examples of structures in which the pores can be in sufficient number and size so as to interconnect across the entire thickness of the porous layer.

In some embodiments, the pores may not interconnect across the entire thickness of the porous layer, but rather may be present at a portion thereof. Thus, in some embodiments, pores may be located on a portion of the porous layer, with other portions of the porous layer having a non-porous texture. Those skilled in the art reading the present disclosure will envision a variety of pore distribution patterns and configurations for the porous layer.

Closed cell foam or fused non-woven materials are illustrative examples of structures in which the pores may not inter-connect across the entire thickness of the porous layer. Where a porous layer of the surgical buttress is fibrous, the fibers may be filaments or threads suitable for knitting or weaving or may be staple fibers, such as those frequently used for preparing non-woven materials. Suitable techniques for making fibrous structures are within the purview of those skilled in the art.

Where a porous layer of the surgical implant or buttress is foam, the porous layer may be formed using any method suitable to forming a foam or sponge including, but not limited to the lyophilization or freeze drying of a composition. Suitable techniques for making foams are within the purview of those skilled in the art.

The origin and types of collagens that may be used to form the porous layer are the same as those indicated above for the non-porous layer. However, the oxidized or non-oxidized collagen may be lyophilized, freeze-dried, or emulsified in the presence of a volume of air to create a foam and then freeze-dried, to form a porous compress.

In some embodiments, a porous layer of the surgical buttress may be made from denatured collagen or collagen which has at least partially lost its helical structure through heating or any other method. The term "denatured collagen" means collagen which has lost its helical structure. The collagen used for the porous layer as described herein may be native collagen or atellocollagen. The collagen may have been previously chemically modified by oxidation, methylation, succinylation, ethylation, or any other known process. The porous layer(s) may enhance the ability of the surgical buttress to absorb fluid, reduce bleeding, and seal the wound. Also, the porous layer(s) may allow for tissue ingrowth to the surgical implant or buttress in place.

Methods of Use

Surgical closure devices like stapling devices have found widespread application in surgical operations where body tissue must be joined or removed. When operating on thin tissue, such as thin emphysematous lung tissue, it is important to effectively seal the tissue which can be particularly prone to air leakage. Preventing or reducing air leakage can significantly decrease post-operative recovery time. Thus, it would be advantageous to provide an apparatus for positioning and affixing a surgical mesh or surgical buttress that would sealing at the surgical site or could affix drug eluting materials at the site of resection leading to better patient outcomes. In the case of removal of infected or malignant tissue, the device would affix a drug-eluting biocompatible or biodegradable implant to the resection margin to administer drug over a period of time. Sustained, long-term delivery of drug would result in superior efficacy with reduced systemic dose-limiting toxicity.

Other diseases that may exhibit post-surgical locally recurrent disease include head and neck cancer, breast cancer lumpectomy, anal cancer and bladder cancer. Devices that employ a surgical mesh or surgical buttress for localized drug delivery would be particularly suited to treatment of such diseases that exhibit local post-surgical recurrence.

Operation of a surgical system falling within the scope of this invention is described below. The cartridge housing the implant material (e.g., surgical mesh or buttress material) and fixation elements, which is located at the head of the introducer, can be introduced through a standard laparoscopic trocar or used during any open procedure. The clinician navigates the distal end of cartridge assembly through to the desired anatomic site and positions the cartridge assembly using the articulation mechanism of the introducer. The cartridge is then deployed from the distal end of the introducer and articulated relative to the shaft using controls in the handle of the introducer in a controlled manner to accurately grasp the segment of tissue to which the implant material will be affixed. The clinician grasps the desired tissue using by directing the element of the controls from the ergonomic proximal handle and then actuates the device with another control to secure the implant to the tissue. The clinician can then disengage the introducer and remove it from the body leaving behind the implant material affixed to the tissue using the fixation elements.

In some embodiments, the cartridge assembly includes pusher members which are acted upon by a slidably mounted cam bar. Upon movement of the cam bar in the appropriate direction using the actuation mechanism, pusher members exert an upwardly-directed force on fixation devices housed in cartridge assembly. Fixation elements can then close around the target tissue and then with a further reversible actuation by the clinician, penetrate implant fabric (e.g. secured to cartridge assembly by a plurality of pins) and tissue layer. Thereafter, the fixation elements strike the anvil assembly for final fixation. Following actuation, the implant material disengages from the introducer and the introducer is withdrawn from the surgical site, thus leaving behind an implant material affixed to body tissue with a plurality of fixation elements.

Embodiments include methods of delivering and securing a surgical mesh to internal soft or hard tissue of a human or non-human subject using the devices and systems described therein. Some embodiments include methods of localized treatment of internal hard or soft tissue of a human or non-human subject using devices and systems described herein that include surgical mesh with bioactive agents or therapeutic agents. Some embodiments include methods of tissue repair or restoration of internal hard or soft tissue of a human or non-human subject using devices and systems described herein with surgical mesh configured to support cellular ingrowth or osteocyte ingrowth. The surgical mesh may include one or more therapeutic agents that promote cellular ingrowth into the mesh.

The devices for affixing a surgical mesh to tissue described herein can be utilized therapeutically and/or cosmetically. For example, the implant (e.g., surgical mesh and affixation elements or clamp) in any form described herein can be used to diagnose, promote healing of and/or inhibit disease by targeting bioactive agent delivery to local and regional areas, or by physical means due to its composition and design. Therapeutic or diagnostic utility of the implant (e.g., surgical mesh and affixation elements or clamp) can be achieved by physical means (e.g., buttress, promoting tissue ingrowth, etc.), chemical means (anti-infective, anti-inflammatory growth promoting compound, etc.), interaction with external excitation (e.g., microwave, infrared (IR), or ultraviolet (UV) radiation, etc.) or a combination of the aforementioned.

While this invention has been disclosed herein in connection with certain embodiments and certain structural and procedural details, it is clear that changes, modifications or equivalents can be used by those skilled in the art. Accordingly, such changes within the principles of this invention are intended to be included within the scope of the claims below.

The invention claimed is:

1. A method comprising:
providing a biocompatible surgical fabric and plurality of fixation elements attached to the biocompatible surgical fabric, the biocompatible surgical fabric having a first surface, a first end portion, and a second end portion;
positioning, using an introducer, the biocompatible surgical fabric with the attached plurality of fixation elements over a surgical margin of tissue with the first surface of the biocompatible surgical fabric at least partially covering a first surface of the surgical margin and at least partially covering a second surface of the surgical margin, wherein the first surface of the surgical margin faces away from the second surface of the surgical margin; and
after positioning the biocompatible surgical fabric with the attached plurality of fixation elements over the surgical margin of tissue, affixing the biocompatible surgical fabric to the surgical margin using the plurality of fixation elements by actuation of an actuation mechanism using the introducer, wherein the plurality of fixation elements secure the biocompatible surgical fabric to the surgical margin upon actuation of the actuation mechanism, and wherein the plurality of fixation elements are attached to the biocompatible surgical fabric prior to actuation of the actuation mechanism.

2. The method of claim 1, wherein the method is a method of treatment of tissue of a subject;
wherein the biocompatible surgical fabric comprises a therapeutic agent comprising one or more of a chemotherapeutic agent, an antibiotic agent, an antiviral agent, an anti-inflammatory agent, a cytokine, a targeting compound, an immunotoxin, anti-tumor antibodies, an anti-angiogenic agent, an anti-edema agent, a radiosensitizer, a nucleic acid, and a prodrug or analog; and
wherein the method further comprises delivering the therapeutic agent from the biocompatible surgical fabric to surrounding tissues via diffusion of the therapeutic agent.

3. The method of claim 1, wherein the surgical margin is previously stapled, sutured, or glued resection line tissue, and wherein positioning the first surface of the biocompatible surgical fabric with the attached plurality of fixation elements over the previously stapled, sutured, or glued resection line tissue comprises positioning the first surface of the biocompatible surgical fabric at least partially covering staples, sutures or glue.

4. The method of claim 1, where the first end portion of the biocompatible surgical fabric includes a first edge and the second end portion of the biocompatible surgical fabric includes a second edge; and
wherein the introducer includes or is coupleable to a clamp including a first clamping surface opposite a second clamping surface with the second surface of the biocompatible surgical fabric at the first end portion in contact with the first clamping surface and the second surface of the biocompatible surgical fabric at the second end portion in contact with the second clamping surface, with the first surface of the biocompatible surgical fabric at the first end portion facing and separated from the first surface of the biocompatible surgical fabric at the second end portion by a gap and with the first edge of the first end portion separated from the second edge of the second end portion by the gap;
wherein affixing the biocompatible surgical fabric to the surgical margin using the plurality of fixation elements comprises actuating the clamp using the introducer to affix the biocompatible surgical fabric to the tissue using the plurality of fixation elements.

5. The method of claim 4, wherein the method is a method of treatment of tissue of a subject;
wherein the biocompatible surgical fabric comprises a therapeutic agent comprising one or more of a chemotherapeutic agent, an antibiotic agent, an antiviral agent, an anti-inflammatory agent, a cytokine, a targeting compound, an immunotoxin, anti-tumor antibodies, an anti-angiogenic agent, an anti-edema agent, a radiosensitizer, a nucleic acid, and a prodrug or analog; and
wherein the method further comprises delivering the therapeutic agent from the biocompatible surgical fabric to surrounding tissues via diffusion of the therapeutic agent.

6. The method of claim 4, wherein the surgical margin is previously stapled, sutured, or glued resection line tissue, and wherein positioning the first surface of the biocompatible surgical fabric with the attached plurality of fixation elements over the previously stapled, sutured, or glued resection line tissue comprises positioning the first surface of the biocompatible surgical fabric at least partially covering staples, sutures or glue.

7. The method of claim 4, wherein the surgical margin is previously stapled, sutured, or glued resection line tissue, and
wherein the clamp is configured to receive the previously stapled, sutured, or glued resection line tissue in the gap and configured to position the first surface of the biocompatible surgical fabric at least partially covering the previously stapled, sutured, or glued resection line tissue.

8. The method of claim 4, wherein the surgical margin is secured prior to positioning the first surface of the biocompatible surgical fabric over the surgical margin.

9. The method of claim 4, wherein the surgical margin is resection line tissue and the resection line tissue of the surgical margin is secured prior to positioning the first surface of the biocompatible surgical fabric over the surgical margin.

10. The method of claim 4, wherein the biocompatible surgical fabric comprises acellular collagen.

11. The method of claim 1, wherein the biocompatible surgical fabric includes a bioactive agent; and
wherein the bioactive agent comprises one or more of a chemotherapeutic agent, an antibiotic agent, an antiviral agent, an anti-inflammatory agent, a cytokine, a targeting compound, an immunotoxin, anti-tumor antibodies, an anti-angiogenic agent, an anti-edema agent, a radiosensitizer, a nucleic acid, and a prodrug or analog.

12. The method of claim 1, wherein the method is a method of treatment of tissue of the subject;
wherein the biocompatible surgical fabric comprises a therapeutic agent; and
wherein the method further comprises delivering the therapeutic agent from the biocompatible surgical fabric to surrounding tissues via diffusion of the therapeutic agent.

13. The method of claim 1, wherein the method is a method of treating a cancer or reducing a risk of recurrence of a cancer in the subject;
wherein the surgical margin results from removal at least a portion of a cancer;
wherein the biocompatible surgical fabric comprises a cancer treating agent; and
wherein the method further comprises delivering the cancer treating agent from the biocompatible surgical fabric to surrounding tissues via diffusion of the cancer treating agent.

14. The method of claim 13, wherein the cancer is lung cancer.

15. The method of claim 1, wherein one or both of the biocompatible surgical fabric and plurality of fixation elements comprise a visualization agent; and
wherein the method further comprises visualizing the biocompatible surgical fabric or plurality of fixation elements after positioning the biocompatible surgical fabric over the surgical margin.

16. The method of claim 15, wherein the biocompatible surgical fabric comprises the visualization element.

17. The method of claim 1, wherein the method is a method of tissue repair or restoration of tissue of the subject; and
wherein the method further comprises promoting cellular ingrowth of surrounding tissues into the biocompatible surgical fabric.

18. The method of claim 17, wherein the biocompatible surgical fabric includes one or more therapeutic agents that promote cellular ingrowth into the biocompatible surgical fabric.

19. The method of claim 17, wherein the biocompatible surgical fabric is configured for functional support of osteocyte ingrowth.

20. The method of claim 1, wherein the biocompatible surgical fabric comprises or functions as a surgical buttress configured for tissue reinforcement.

21. The method of claim 1, wherein the provided biocompatible surgical fabric and plurality of fixation elements include a surgical glue or surgical sealant disposed on the first surface of the biocompatible surgical fabric at the first end portion and/or the second end portion.

22. The method of claim 1, wherein the surgical margin is secured prior to positioning the first surface of the biocompatible surgical fabric over the surgical margin.

23. The method of claim 1, wherein the surgical margin is resection line tissue and the resection line tissue of the surgical margin is secured prior to positioning the first surface of the biocompatible surgical fabric over the surgical margin.

24. The method of claim 1, wherein the biocompatible surgical fabric comprises acellular collagen.

25. The method of claim 1, where the first end portion of the biocompatible surgical fabric includes a first edge, the second end portion of the biocompatible surgical fabric includes a second edge, and the biocompatible surgical fabric has a length measured along the first edge; and
wherein the biocompatible surgical fabric is positioned with the biocompatible surgical fabric wrapping around an edge of the surgical margin and with the first edge of the biocompatible surgical fabric extending roughly parallel to the edge of the surgical margin.

26. The method of claim 1, wherein the plurality of fixation elements includes a glue.

* * * * *